United States Patent [19]
Li

[11] Patent Number: 5,431,665
[45] Date of Patent: Jul. 11, 1995

[54] COMEDO EXTRACTING TOOL

[76] Inventor: Yang C. Li, 3F., No. 33~35, Tzu Chih Steet, Hsin Chuang City, Taipei Hsien, Taiwan

[21] Appl. No.: 285,127

[22] Filed: Aug. 2, 1994

[51] Int. Cl.⁶ ........................ A61B 17/28; A61B 19/00
[52] U.S. Cl. ..................... 606/131; 606/205; 606/211
[58] Field of Search ............ 606/1, 131, 133, 205–211; 294/99.2; 132/73, 75.3, 76.2

[56] References Cited
U.S. PATENT DOCUMENTS

| | | | |
|---|---|---|---|
| 834,683 | 10/1906 | Severin | 606/131 |
| 896,338 | 8/1908 | Tolman | 606/131 |
| 906,085 | 12/1908 | Tolman | 606/131 |
| 1,842,403 | 1/1932 | Munsoker et al. | 606/131 |
| 2,818,866 | 1/1958 | Thomas | 606/211 |

Primary Examiner—Stephen C. Pellegrino
Assistant Examiner—Glenn Dawson

[57] ABSTRACT

A comedo extracting tool having a comedo extractor at one end, a clap forceps at an opposite end, and a flat handle connected between the comedo extractor and the clamp forceps. The comedo extractor has an oblong opening in the center, the width of the oblong opening reducing gradually toward the handle. The clamp forceps terminates in a pair of pointed hooks.

1 Claim, 5 Drawing Sheets

COMEDO EXTRACTING TOOL

BACKGROUND OF THE INVENTION

The present invention relates to a comedo extracting tool which has a comedo extractor at one end and a clamp forceps with pointed hooks at an opposite end.

For removing comedones or pimples out of the skin, a comedo extractor may be used. FIG. 1 shows a commercially available comedo extractor which is an elongated handle having a taper hole 21 at one end and a ring 22 at an opposite end. When the taper hole 21 or ring 22 is placed on the skin around the comedo or pimple, a downward pressure is employed to the skin through the comedo extractor causing the comedo or pimple extracted out of the skin. This structure of comedo extractor is not orthopedically engineered because the two opposite ends (the taper hole 21 and the ring 22) of the comedo extractor are approximately disposed on the same plane, therefore it is difficult to employ downward pressure to the skin without causing a hurt. Furthermore, because the ring 22 and the taper hole 21 defines a respective rounded passage, they do not fit comedones and pimples of different sizes. During the extracting process, excessive pressure tends to be employed to the skin causing a big area in the skin injured.

SUMMARY OF THE INVENTION

The present invention has been accomplished to provide a comedo extracting tool which eliminates the aforesaid drawbacks. According to one aspect of the present invention, the comedo extracting tool comprises a comedo extractor at one end, a clamp forceps at an opposite end, and a flat handle connected between the comedo extractor and the clamp forceps. According to another aspect of the present invention, the clamp forceps terminate in a pair of pointed hooks for clamping as well as for piercing. According to still another aspect of the present invention, the comedo extractor is shaped like a spoon having a smoothly curved bottom surface and defining an oblong opening in the center, wherein the width of the oblong opening reduces gradually toward the handle. Therefore, the comedo extractor is suitable for extracting comedones of different sizes.

DETAILED DESCRIPTION OF THE PREFERRED EMBODIMENT

Figure 1:
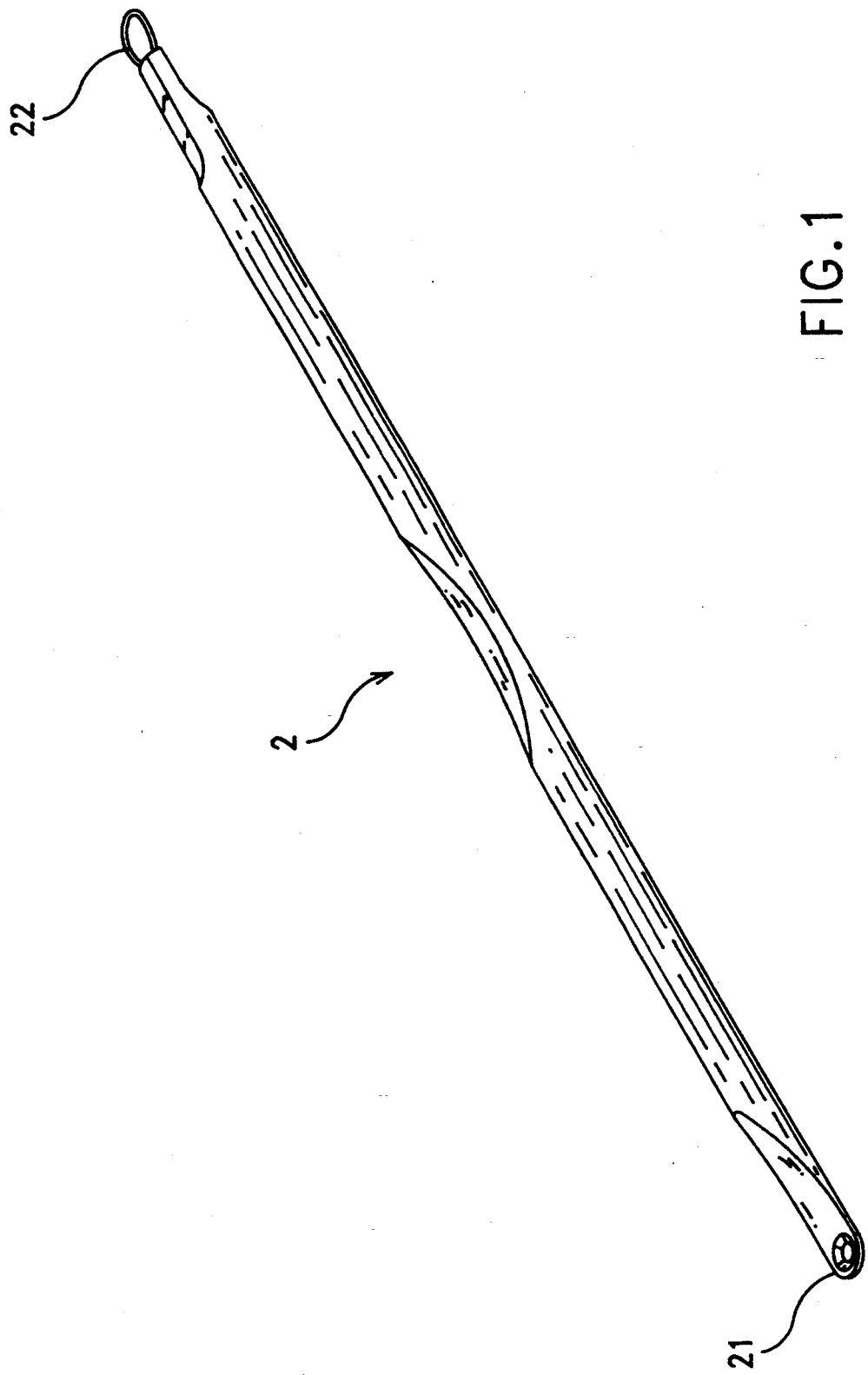
FIG. 1 shows a comedo extractor according to the prior art.
Figure 2:
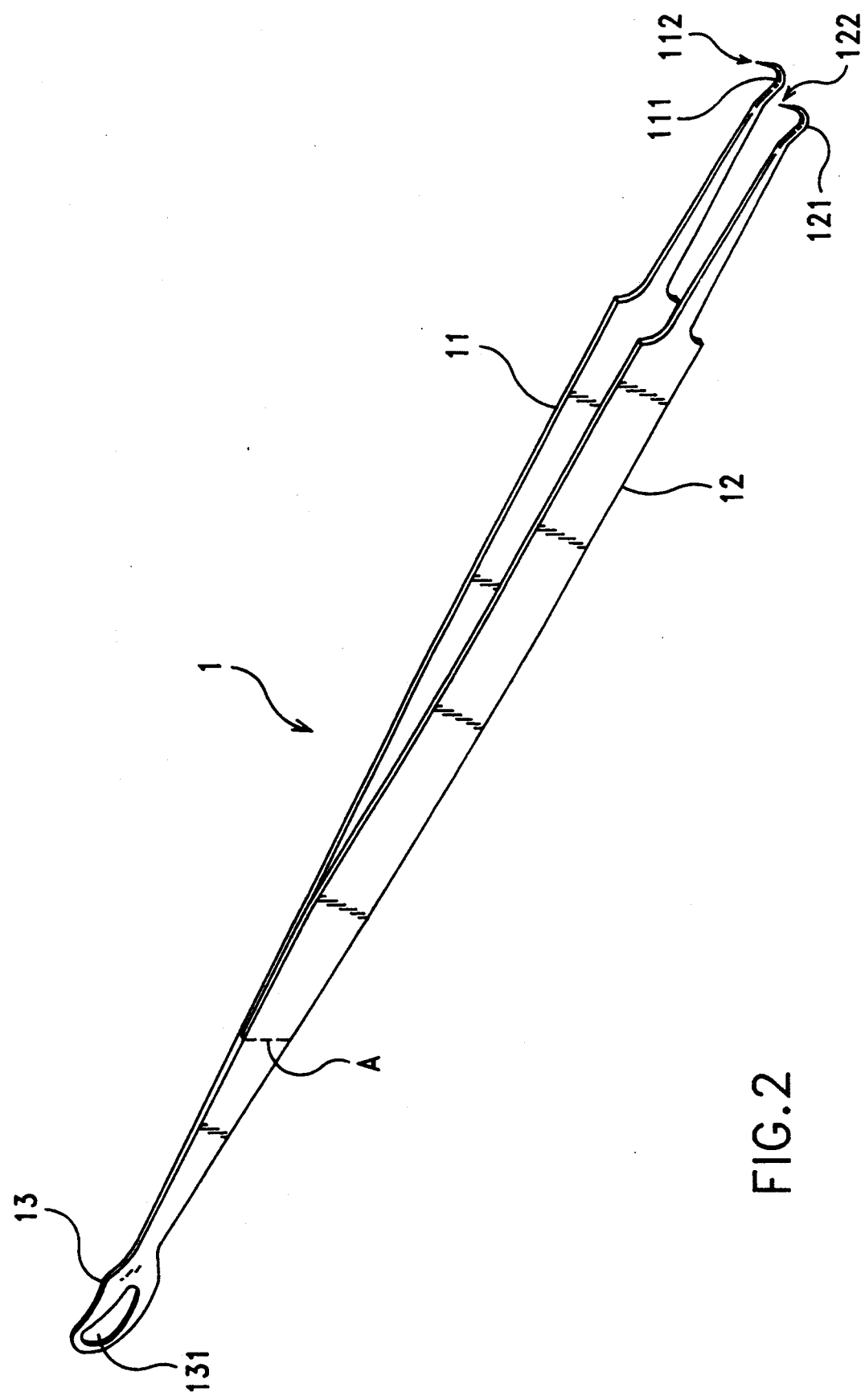
FIG. 2 shows a comedo extracting tool according to the present invention.

Referring to FIG. 2, a tool 1 in accordance with the present invention is comprised of a flat handle having one end terminating in a spoon-like comedo extracting plate 13 and an opposite end A welded with two symmetrical clamping tongues 11 and 12. The length of the clamping tongues 11 and 12 is about two third of the total length of the tool 1. The clamping tongues 11 and 12 respectively terminate in a hook 111 or 121 having a pointed tip 112 or 122. When the clamping tongues 11 and 12 are pressed inwards toward each other, the hooks 111 and 121 are forced to hold down the object. The pointed tips 112 and 122 of thee hooks 111 and 121 of the clamping tongues 11 and 12 can be used to pierce the skin, or a pimple. The comedo extracting plate 13 has a smoothly curved bottom surface, defining an oblong opening 131 in the center for extracting comedones out of the skin. The width of the oblong opening 131 reduces gradually toward the end adjacent to the clamping tongues 11 and 12.

Figure 3:
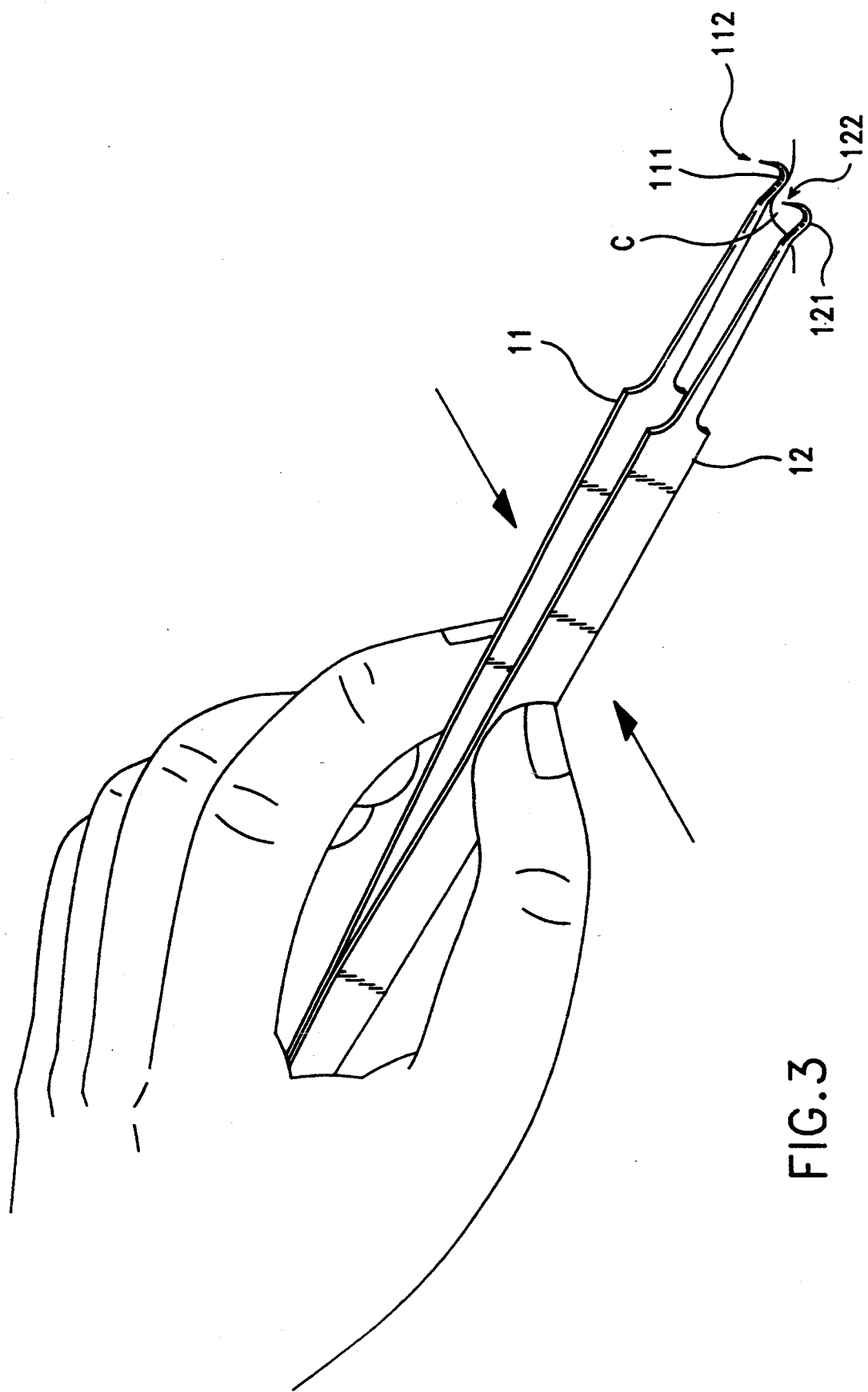
FIG. 3 shows the clamping tongues of the comedo extracting tool of FIG. 2 pressed inwards and the hooks of the clamping tongues clamped on the pimple.

Referring to FIG. 3, by pressing the clamping tongues 11 and 12 inwards toward each other, the hooks 111 and 121 are forced to squeeze the pimple C, causing the pimple C expelled out of the skin. Because the hooks 111 and 121 are clamped on a limited area around the pimple, removing the pimple out of the skin does not hurt other tissues.

Figure 4:
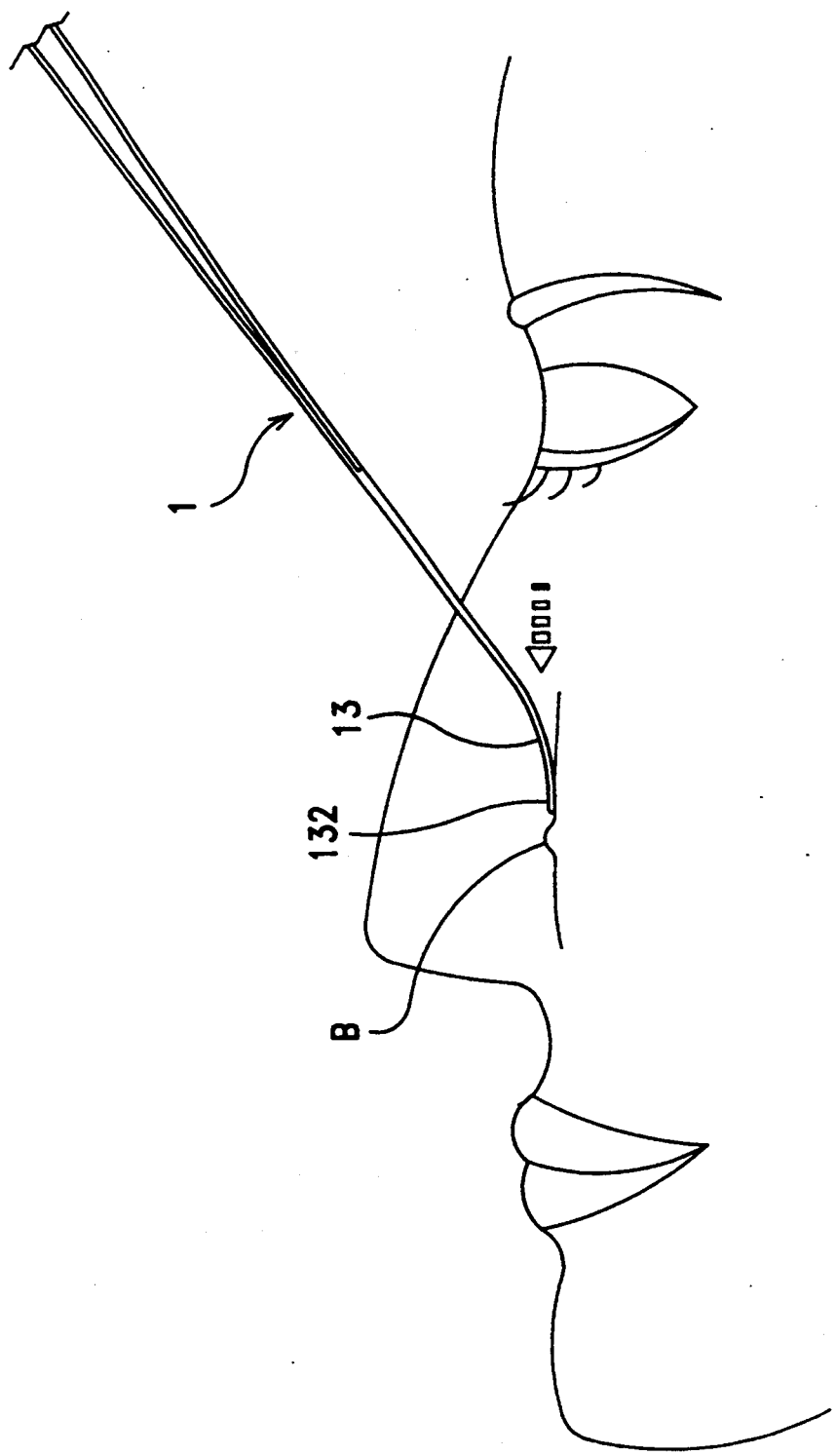
FIG. 4 shows the comedo extracting plate of the comedo extracting tool of FIG. 2 pressed on the skin.

Referring to FIG. 4, the comedo extracting plate 13 has a smoothly curved bottom surface, therefore the skin will not be injured when the comedo extracting plate 13 is pressed on the skin and moved toward the comedo B to be extracted.

Figure 5:
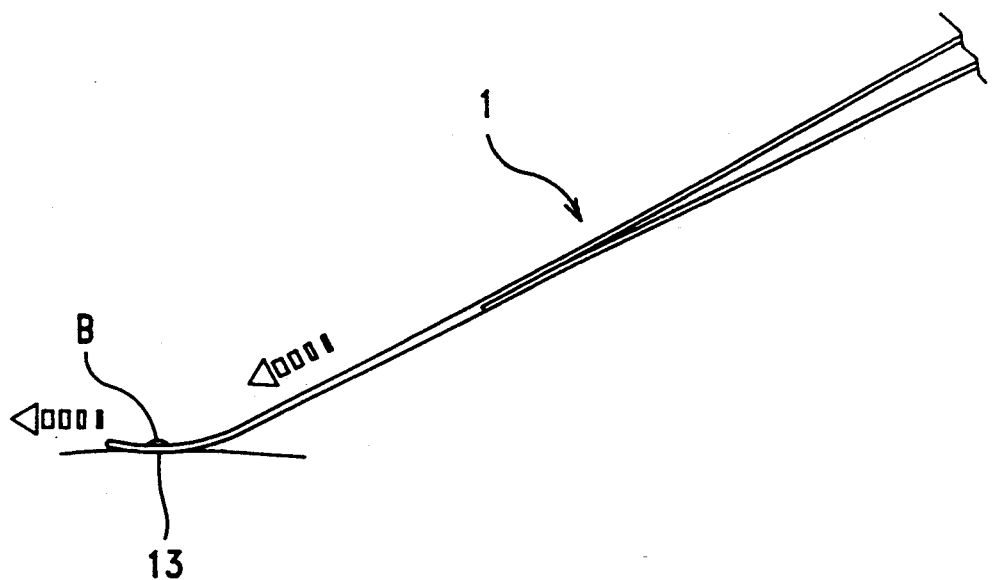
FIG. 5 is similar to FIG. 4 but showing the pimple retained within the oblong opening of the comedo extractor.
Figure 6:
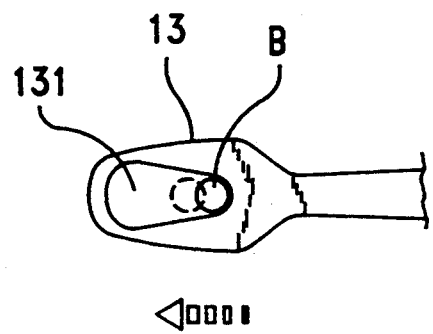
FIG. 6 is a top view of the comedo extracting plate shown in FIG. 5, showing the pimple extracted out of the skin.

Referring to FIGS. 5 and 6, when the comedo extracting plate 13 is pressed on the skin around the comedo B to be extracted, it is moved forward to extract the comedo B out of the skin. Because the width of the oblong opening 131 reduces gradually toward the end adjacent to the clamping tongues 11 and 12, the squeezing force is gradually increased when the comedo extracting plate 13 is moved forwards, therefore the comedo B can be easily extracted out of the skin. If the comedo cannot be extracted out of the skin, the pointed tip 112 or 122 can be used to pierce a hole on the skin for permitting the comedo to be conveniently extracted out of the skin by the comedo extracting plate 13.

What is claimed is:

1. A comedo extracting tool comprising a flat handle, a spoon-like comedo extracting plate at one end of said handle, a clamp forceps comprising two symmetrically clamping tongues longitudinally extending from an opposite end of said handle and each clamping tongue terminating in a respective pointed hook, said spoon-like comedo extracting plate defining an oblong opening in the center of said comedo extracting plate, the width of said oblong opening gradually reducing toward said handle.

* * * * *